US012637383B2

(12) United States Patent
Kojima et al.

(10) Patent No.: US 12,637,383 B2
(45) Date of Patent: May 26, 2026

(54) METHOD OF PRODUCING GLASS-CERAMIC BLANK, AND GLASS-CERAMIC BLANK

(71) Applicant: GC CORPORATION, Shizuoka (JP)

(72) Inventors: Kenji Kojima, Itabashi-ku (JP); Koji Yamamoto, Itabashi-ku (JP)

(73) Assignee: GC CORPORATION, Sunto-gun (JP)

( * ) Notice: Subject to any disclaimer, the term of this patent is extended or adjusted under 35 U.S.C. 154(b) by 146 days.

(21) Appl. No.: 18/032,728

(22) PCT Filed: Mar. 10, 2022

(86) PCT No.: PCT/JP2022/010602
§ 371 (c)(1),
(2) Date: Apr. 19, 2023

(87) PCT Pub. No.: WO2022/209706
PCT Pub. Date: Oct. 6, 2022

(65) Prior Publication Data
US 2023/0303419 A1 Sep. 28, 2023

(30) Foreign Application Priority Data
Mar. 31, 2021 (JP) ................................. 2021-061439

(51) Int. Cl.
| | |
|---|---|
| *C03B 11/14* | (2006.01) |
| *A61C 13/00* | (2006.01) |
| *A61K 6/836* | (2020.01) |
| *C03B 19/06* | (2006.01) |
| *C03B 27/012* | (2006.01) |
| *C03C 4/00* | (2006.01) |
| *C03C 21/00* | (2006.01) |

(52) U.S. Cl.
CPC .......... *C03B 11/14* (2013.01); *A61C 13/0022* (2013.01); *C03B 19/06* (2013.01); *C03B 27/012* (2013.01); *C03C 21/00* (2013.01); *A61K 6/836* (2020.01); *C03B 2215/06* (2013.01); *C03C 4/0021* (2013.01)

(58) Field of Classification Search
CPC ....... C03C 10/00; C03C 4/0021; C03B 19/06; C03B 11/14; A61C 13/0022; A61K 6/836
See application file for complete search history.

(56) References Cited

U.S. PATENT DOCUMENTS

| | | | | |
|---|---|---|---|---|
| 4,433,959 | A | * | 2/1984 | Faunce .................... A61C 5/20 106/35 |
| 6,114,054 | A | * | 9/2000 | Klein ...................... C04B 41/52 428/689 |
| 2008/0064011 | A1 | * | 3/2008 | Rheinberger ...... A61C 13/0022 433/215 |
| 2010/0221683 | A1 | * | 9/2010 | Franke ..................... A61K 6/15 252/182.34 |
| 2014/0120297 | A1 | * | 5/2014 | Reinshagen ....... A61C 13/0022 264/16 |
| 2014/0328746 | A1 | * | 11/2014 | Yamada ................. C01G 25/02 423/608 |
| 2015/0111717 | A1 | * | 4/2015 | Gabel ..................... C03C 3/087 501/32 |
| 2015/0140274 | A1 | * | 5/2015 | Burke ..................... C03C 3/085 264/19 |
| 2015/0335407 | A1 | * | 11/2015 | Korten ................ A61C 13/082 264/20 |
| 2015/0374465 | A1 | * | 12/2015 | Bürke ..................... A61C 5/73 433/201.1 |
| 2016/0081777 | A1 | * | 3/2016 | Yamada ............... A61C 13/083 428/220 |
| 2017/0128174 | A1 | * | 5/2017 | Mayr ....................... A61K 6/78 |
| 2017/0157645 | A1 | * | 6/2017 | Wolz .................. A61C 13/0006 |
| 2017/0183270 | A1 | * | 6/2017 | Wondraczek ...... A61C 13/0022 |
| 2018/0028293 | A1 | | 2/2018 | Kadobayashi et al. |
| 2018/0104031 | A1 | * | 4/2018 | Vollmann .......... A61C 13/0003 |
| 2019/0099244 | A1 | * | 4/2019 | Vollmann ............. A61C 13/083 |
| 2019/0202731 | A1 | * | 7/2019 | Yamamoto .............. C03C 3/097 |
| 2020/0283341 | A1 | * | 9/2020 | Ushio ..................... B32B 18/00 |
| 2020/0317561 | A1 | * | 10/2020 | Arnold ................. A61C 13/083 |
| 2022/0192804 | A1 | | 6/2022 | He et al. |

FOREIGN PATENT DOCUMENTS

| | | | | | |
|---|---|---|---|---|---|
| CN | 110981204 | A | * | 4/2020 | ............. C03C 10/00 |
| CN | 112159082 | A | * | 1/2021 | ............. B32B 17/06 |
| JP | 2006321689 | A | * | 11/2006 | ............... C03C 4/12 |
| JP | 2008-068079 | A | | 3/2008 | |
| JP | 2018-015364 | A | | 2/2018 | |
| JP | 2020-169118 | A | | 10/2020 | |
| WO | WO-2020129918 | A1 | * | 6/2020 | .......... C04B 35/486 |
| WO | 2020/210956 | A1 | | 10/2020 | |
| WO | WO-2020210958 | A1 | * | 10/2020 | .......... C03C 4/0021 |
| WO | WO-2020230646 | A1 | * | 11/2020 | |

OTHER PUBLICATIONS

International Search Report for PCT/JP2022/010602 dated May 31, 2022 [PCT/ISA/210].

* cited by examiner

*Primary Examiner* — Erin Snelting
*Assistant Examiner* — Steven S Lee
(74) *Attorney, Agent, or Firm* — Sughrue Mion, PLLC

(57) ABSTRACT

Provided is a method of producing a glass-ceramic blank including: preparing plural glass-ceramic powders, laminating the glass-ceramic powders, so that colors of any adjacent layers of the powders are the same as or approximate to each other, and so that said any adjacent layers are different in total light transmittance, and pressure-molding the laminated powders; heating, at 500° C. to 800° C., a laminate obtained by the pressure molding to degrease the laminate; immersing an entire of the laminate after the degreasing in a colorant solution including a single-colored metal ion; and heat-treating, at higher than 750° C. and 1000° C. or lower, the laminate having immersed in the colorant solution.

4 Claims, No Drawings

METHOD OF PRODUCING GLASS-CERAMIC BLANK, AND GLASS-CERAMIC BLANK

CROSS REFERENCE TO RELATED APPLICATIONS

This application is a National Stage of International Application No. PCT/JP2022/010602 filed Mar. 10, 2022, claiming priority based on Japanese Patent Application No. 2021-061439 filed Mar. 31, 2021.

TECHNICAL FIELD

The present disclosure relates to a blank that is made from a glass ceramics and that has not been processed into dental restorations yet, and particularly, to a colored glass-ceramic blank.

BACKGROUND

Examples of the method of producing a glass-ceramic blank that is a material for obtaining, by milling, dental restorations include: melt molding of pouring a molten glass into a mold; and powder molding of pulverizing a molten lithium silicate glass, and pressure-molding the powder.

Following recent developments in digital dentistry and a recent increase in demands for all-ceramic restorations, there is a demand for dental restorations to show a natural color gradient closer to natural teeth, and therefore, a natural color gradient in a glass-ceramic blank is also demanded.

In melt molding, coloring is performed by adding a coloring agent before melting. Therefore, a glass-ceramic blank obtained by melt molding is a single color.

In contrast, concerning powder molding, patent literature 1 discloses that powders of different shades are layered, and thereby, show a color gradient. By this method, the color gradient tends to be steplike due to the layering, and a naturally transitioning color gradient is not obtained.

Patent literature 2 discloses that plural liquids of different colors are made to permeate a material formed by solidifying powder in a predetermined order. This method requires plural liquids, and also requires control over the timing and position for the permeation, which take much effort at production.

CITATION LIST

Patent Literature

Patent Literature 1: JP 2008-68079 A
Patent Literature 2: JP 2018-15364 A

SUMMARY OF INVENTION

Technical Problem

In view of the aforementioned problems, an object of the present disclosure is to provide a method of producing a glass-ceramic blank which enables a glass-ceramic blank showing a natural color gradient to be more easily obtained. Another object of the present disclosure is to provide a glass-ceramic blank.

Solution to Problem

A first aspect of the present disclosure is a method of producing a glass-ceramic blank formed by laminating plural layers, the method comprising: preparing plural glass-ceramic powders, laminating the glass-ceramic powders, so that colors of any adjacent layers of the powders are the same as or approximate to each other, and so that said any adjacent layers are different in total light transmittance, and pressure-molding the laminated powders; heating, at 500° C. to 800° C., a laminate obtained by the pressure molding to degrease the laminate; immersing an entire of the laminate after the degreasing in a colorant solution including a single-colored metal ion; and heat-treating, at higher than 750° C. and 1000° C. or lower, the laminate having immersed in the colorant solution.

In the pressure molding in the first aspect, a color difference between said any adjacent layers may be at most 5.5.

In the pressure molding in the first aspect, a difference between said any adjacent layers in total light transmittance may be 0.1% to 8%.

In the first aspect, the total light transmittance may be at least 33%.

A second aspect of the present disclosure is a glass-ceramic blank formed by laminating plural layers, wherein colors of materials themselves are the same as or approximate to each other, and the materials are different in total light transmittance, the materials constituting any adjacent layers among the plural layers.

In the second aspect, a color difference between the materials themselves may be at most 5.5.

In the second aspect, a difference between the materials in total light transmittance may be 0.1% to 8%.

In the second aspect, the total light transmittance may be at least 33%.

Advantageous Effect of Invention

The present disclosure enables a glass-ceramic blank showing a natural color gradient to be obtained.

DESCRIPTION OF EMBODIMENTS

The method of producing a glass-ceramic blank according to the present disclosure is by powder molding. That is, a molten lithium silicate glass is pulverized to yield a powder, and the powder is subjected to pressure molding to yield a glass-ceramic blank. The following is a detailed description.

1. MATERIALS

For producing a glass-ceramic blank according to the present disclosure, the following materials in the following amounts are prepared.

$SiO_2$: 60.0 mass % to 80.0 mass %
$Li_2O$: 10.0 mass % to 20.0 mass %
$Al_2O_3$: 3.0 mass % to 15.0 mass %

Here, $SiO_2$ in an amount outside this range makes it difficult to obtain a homogeneous glass blank. $SiO_2$ is preferably in an amount of 65 mass % to 75 mass %.

$Li_2O$ in an amount outside this range also makes it difficult to obtain a homogeneous glass blank. $Li_2O$ is preferably in an amount of 11 mass % to 17 mass %.

$Al_2O_3$ in an amount less than 3.0 mass % yields the deposition of lithium disilicate as a major crystal phase, and may cause a problem in machinability. When $Al_2O_3$ is in an amount more than 15.0 mass %, lithium disilicate does not constitute the major crystal phase, and may lead to unsatisfaction with mechanical strength (e.g., lithium aluminosilicate is deposited). $Al_2O_3$ is preferably in an amount of 3.0 mass % to 7.0 mass %.

As a material for the glass-ceramic blank, the following compounds that are to be a crystalline nucleating material may be included. The crystalline nucleating material herein is not particularly limited, and any of known crystalline nucleating materials can be widely used. This leads to efficient formation of crystalline nuclei to form a lithium disilicate crystal.

Examples of the crystalline nucleating material include $P_2O_5$, $TiO_2$, $ZrO_2$, $Ta_2O_5$, ZnO, $Nb_2O_5$, $Y_2O_3$ and $La_2O_3$. Such a material can be included in an amount in the range of 0 mass % and 10.0 mass %. It is not necessary that the components shown here are always included, but any of them may be included, as can be seen from the foregoing range including 0 mass %. The same is also applied to the following.

The materials of the glass-ceramic blank may include the following components in addition to the foregoing. All the following components can be included in an amount of 0 mass % to 15 mass % each. The amounts of each of the components are more preferably as follows.

$Na_2O$: 0 mass % to 2.8 mass %
$K_2O$: 0 mass % to 10.0% mass %
CaO: 0 mass % to 3.0 mass %
SrO: 0 mass % to 10.0 mass %
BaO: 0 mass % to 10.0 mass %
MgO: 0 mass % to 3.0 mass %
$Rb_2O$: 0 mass % to 2.8 mass %
$Cs_2O$: 0 mass % to 2.8 mass %
$Fr_2O$: 0 mass % to 2.8 mass %
BeO: 0 mass % to 3.0 mass %
RaO: 0 mass % to 10.0 mass %

These components enable the melting temperature of a material for dental restorations to be adjusted when this material is made. It is noted that when included, these components are preferably included in an amount of 15 mass % or less each because including any of the components in an amount more than the foregoing just leads to a limited improvement in effect.

In view of adjusting translucency, at least one selected from $CeO_2$, $Er_2O_3$ and $Tb_4O_7$ may be also included in an amount of approximately 1 mass % or less.

2. METHOD OF PRODUCING GLASS-CERAMIC BLANK

Hereinafter a method of producing a glass-ceramic blank according to one embodiment will be described. A method of producing a glass-ceramic blank according to the present embodiment S10 (hereinafter may be referred to as "production method S10") includes the steps of: preparing plural powder materials (step S11); making a pressure laminate (step S12); degreasing (step S13); immersion in a colorant solution (step S14); and sintering (step S15). Hereinafter each of the steps will be described.

2.1. Preparing Plural Powder Materials (Step S11)

In step S11, based on the foregoing materials, plural powder materials characterized by color and light transmissivity are prepared. The powder materials can be each obtained by compounding the foregoing materials, melting the compounded materials at 1300° C. to 1600° C., cooling to solidify the resultant, and then, pulverizing the resultant. The pulverizing way and the degree of the pulverization are as known. For example, the particle diameter of the powder can be in the range of 10 μm and 60 μm. Here, the "particle diameter" means a particle diameter (D50) at the 50% integrated value in the volume-based particle diameter distribution measured by a laser diffraction and scattering method.

The characteristics of the color and the light transmissivity of each of the plural powder materials to be prepared are as follows.

[Color]

The plural powder materials to be prepared shall be such that the colors of any powder materials to be laminated to be adjacent to each other in step S12 will be the same as or will approximate to each other. Specifically, the color difference ΔE between any powder materials to be laminated to be adjacent to each other in step S12 among the plural powder materials is preferably at most 5.5.

Here, the color difference ΔE means "color difference $\Delta E^*_{ab}$ in the L*a*b* color space". That is, ΔE is a distance between the colors of any two layers to be laminated to be adjacent to each other in the L*a*b* color space, and is represented by the following formula when the colors of the two layers are defined by $(L^*_1, a^*_1, b^*_1)$ and $(L^*_2, a^*_2, b^*_2)$, respectively: $\Delta E = \{(L^*_2 - L^*_1)_2 + (a^*_2 - a^*_1)_2 + (b^*_2 - b^*_1)^2\}^{0.5}$ The color difference ΔE is measured as follows. Each of the powders to be used is molded into a cylindrical shape to, thereafter, form a test specimen in the same way as the degreasing in step S13 and the sintering in step S15 (the coloring as in step S14 is not performed), and the test specimen is shaped to have a thickness of 1.2 mm by the use of waterproof abrasive paper #1000. That is, the color difference ΔE referred to herein is a color difference between test specimens obtained by molding the powders into cylindrical shapes, and degreasing as in step S13 and heat-treating as the sintering in step S15 the resultants without coloring performed; and means a difference between the shades of the powder materials themselves (which is distinguished from the undermentioned color difference after the coloring of step S14).

Thereafter, the colors of them are measured with a spectrophotometer (SD 7000: manufactured by Nippon denshoku industries co., ltd.). The color difference ΔE is calculated by the foregoing formula as the Euclidean distance between the obtained color coordinates (the color coordinates in the CIE 1976 L*a*b* color space conforming to JIS Z 8781-4).

[Light Transmissivity]

The plural powder materials to be prepared shall be different in light transmissivity. Specifically, any powder materials to be laminated to be adjacent to each other in step S12 among the plural powder materials are different in total light transmittance.

The total light transmittance is measured with a haze meter (NDH 5000: manufactured by Nippon denshoku industries co., ltd.) by a method conforming to JIS K 7361; and can be defined as the total of the diffuse transmittance and the in-line transmittance for CIE standard illuminant D65 as an incident light.

In the present disclosure, in the same manner as for the measurement of the color difference, the total light transmittance of an object obtained by molding each of the powders to be used into a cylindrical shape to, thereafter, form a test specimen in the same way as the degreasing in step S13 and the sintering in step S15 (the coloring as in step S14 is not performed), and shaping the test specimen to have a thickness of 1.2 mm by the use of waterproof abrasive paper #1000 is used. That is, the total light transmittance referred to herein is the total light transmittance of a test specimen obtained by molding each of the powders into a cylindrical shape, and degreasing as in step S13 and heat-treating as the sintering in step S15 the resultant without coloring performed; and is based on the total light transmittance of each of the powder materials themselves.

The difference between powder materials of any adjacent layers in total light transmittance is not particularly limited, but is preferably 0.1% to 8%, more preferably 0.1% to 6%, and further preferably 0.1% to 3%.

The magnitude of the total light transmittance of each of the plural powder materials is not particularly limited. Preferably, the total light transmittance of at least one of the materials is at least 33%, and more preferably, that of each of all the materials is at least 33%.

2.2. Making Pressure Laminate (Step S12)

In step S12, the plural powder materials obtained in step S11 are laminated in order in a mold, and the laminated materials are subjected to pressure molding to yield a pressure laminate.

More specifically, step S12 is carried out by mixing each of the powder materials with a resin that serves as a binder, and laminating the mixtures in order in a mold, and thereafter, pressing the laminated mixtures.

The binder is not particularly limited as long as being a resin that burns down by heating at 500° C. to 800° C., and preferred examples thereof include acrylic resins. In this embodiment, OLYCOX KC-1700P (from Kyoeisha chemical co., ltd.) is used.

The pressing can be performed with, for example, a uniaxial press at approximately 10 MPa or more and lower than 20 MPa, preferably at 10 MPa to 18 MPa.

2.3. Degreasing (Step S13)

In step S13, the pressure laminate obtained in step S12 is heated, so that the binder resin included in the pressure laminate is removed (degreasing). The heating temperature is not particularly limited, and is preferably approximately 500° C. to 800° C. Among them, in view of smooth progress in crystallization of lithium metasilicate, the heating is more preferably performed at approximately 700° C. because this crystallization starts occurring at 680° C.

2.4. Immersion in Colorant Solution (Step S14)

In step S14, the degreased pressure laminate obtained in step S13 is immersed in a colorant solution to yield a colored pressure laminate.

Here, the colorant solution may be a single color, and an example thereof is a mixture of a metal ion as a coloring agent with a solvent.

The solvent here is not particularly limited as long as the coloring agent is soluble therein, and examples thereof include distilled water and alcohols (methanol and ethanol).

The coloring agent here is not limited either as long as being a suitable metal ion. Examples of the coloring agent include those included in metal oxides used as coloring agents for lithium silicate glass ceramics; and more specific examples thereof include salts including metals such as Ce, Er, Fe, Mn, Tb and V. Examples of these salts include erbium acetate, and cerium acetate.

Other than the foregoing, polyethylene glycol, polypropylene glycol, or the like may be included as a permeability modifier that improves permeability to the degreased pressure laminate if necessary. A trace of hydrochloric acid may be also included. This makes it easy to dissolve the metallic salt in the solvent.

The incorporation is not particularly limited. For example, the solvent can be 70 mass % to 90 mass %, the coloring agent can be 0.1 mass % to 20 mass %, and the permeability modifier can be 0 mass % to 15 mass %.

Permeation is preferably performed by immersing the entire degreased pressure laminate in the colorant solution. The immersion may be performed at an ambient temperature, and is preferably performed in a range of 10° C. and 40° C. The immersing time is preferably at least 1 minute. The upper limit of the immersing time is not particularly limited, and is preferably at most 60 minutes because the immersion for more than this time hardly influences the result.

2.5. Sintering (Step S15)

In step S15, the colored pressure laminate obtained in step S14 is heat-treated to sinter. Thereafter, the resultant is cooled to yield a glass-ceramic blank.

The heat treatment is maintained for a predetermined time at higher than 750° C. and 1000° C. or lower. This can lead to the growth of the crystal of lithium disilicate to yield a lithium disilicate blank having a major crystal phase of lithium disilicate. The maintaining time is preferably at least 1 minute, and further preferably at least 3 minutes. The upper limit of this time is not particularly limited, and can be at most 3 hours.

3. GLASS-CERAMIC BLANK

The glass-ceramic blank obtained by the foregoing production method S10 is a columnar blocklike material such as a prism and a cylinder, or a planar blocklike material such as a square plate or a disk. A dental restoration can be made by deforming or shaving this by machining such as milling.

The color difference between any adjacent layers of the obtained glass-ceramic blank is preferably at most 8. Preferably, said any adjacent layers are different in total light transmittance. It is as described above that the color difference between any adjacent layers in the obtained glass-ceramic blank is different from the aforementioned color difference concerning the powder materials.

Preferably, the coloring agent included in the glass-ceramic blank is the same at the uniform concentration in the entire blank.

4. EFFECT ETC

According to the above-described method of producing a glass-ceramic blank, only immersion in a single-colored colorant solution enables a glass-ceramic blank showing a natural color gradient like natural teeth to be efficiently produced.

In addition, using powder materials such that any adjacent layers satisfy the above-described color and light transmissivity conditions can offer a glass-ceramic blank showing a natural color gradient like natural teeth.

The difference between any materials to be adjacent layers among the powder materials to be used in total light transmittance is made to be 0.1% to 8%, which makes a color gradient between the layers look more natural.

Further, the total light transmittance of at least one, more preferably each of all the powder materials to be used is made to be at least 33%, which further makes a color gradient between the layers look natural. This also allows the coloring in step S14 to be more smoothly performed.

5. EXAMPLES

In the examples, glass-ceramic blanks were made in combination with plural powders of different characteristics (powder A to powder J), and tests were done.

5.1. Preparing Powders

Table 1 shows the powders prepared based on step S11. Table 1 also shows the color, and the total light transmittance of each of the powders, which was measured by the aforementioned method.

The powders included the following components in amounts in different ranges from each other.

$SiO_2$: 69.8 mass % to 71.2 mass %
$Li_2O$: 11.2 mass % to 13.5 mass %
$Al_2O_3$: 4.3 mass % to 5.3 mass %
$P_2O_5$: 3.0 mass % to 7.3 mass %
$Na_2O$: 1.2 mass % to 1.6 mass %
$K_2O$: 1.8 mass % to 2.4 mass %
SrO: 0 mass % to 1.7 mass %
$TiO_2$: 0 mass % to 0.5 mass %
$ZrO_2$: 1.8 mass % to 3.2 mass %

CeO$_2$: 0.1 mass % to 0.2 mass %

Tb$_4$O$_7$: 0.4 mass % coloring agent: 0.2 mass % for each of powder H, powder I and powder J only The powder materials were each obtained by compounding the foregoing materials, melting the compounded materials at 1300° C. to 1600° C., cooling to solidify the resultant, and then, pulverizing the resultant. The particle diameter of the obtained powders was 36.53 nm in terms of D50.

In the step based on step S15, each of the pressure laminates having immersed in the colorant solution was heated at 880° C. for 1 hour to sinter.

5.3. Evaluation and Results

Table 2 shows evaluation items and results. The items were as follows.

TABLE 1

|  | Powder A | Powder B | Powder C | Powder D | Powder E | Powder F | Powder G | Powder H | Powder I | Powder J |
|---|---|---|---|---|---|---|---|---|---|---|
| Color | white | white | white | white | white | white | white | A1 | B1 | A2 |
| Total light transmittance (%) | 34.98 | 37.67 | 42.82 | 45.59 | 48.24 | 32.96 | 31.14 | 46.72 | 42.95 | 39.76 |

Here, the color A1 in the powder H, the color B1 in the powder I, and the color A2 in the powder J were based on the names in the color samples of a VITA classical shade guide (manufactured by Vita).

5.2. Making Glass-Ceramic Blank

The prepared powders were combined to be the layer structures shown in table 2 (for example, "A+B" means that the layer of the powder A and the layer of the powder B were laminated) to form glass-ceramic blanks based on steps S12 to S14. The conditions in each of the steps were as follows.

In the step based on step S12, 5 mass % of OLYCOX KC-1700P (from Kyoeisha chemical co., ltd.) was used as a binder to be mixed with each of the powder materials. Then, pressing was performed with a uniaxial press at 15 MPa in applied pressure.

In the step based on step S13, the obtained pressure laminates were each heated at 700° C. for 10 hours to be degreased.

In the step based on step S14, the degreased pressure laminates were each immersed in a colorant solution at 23°

[Color Difference ΔE]

The color difference ΔE between the adjacent layers of the prepared powder materials themselves was measured by the aforementioned method.

[Difference in Total Light Transmittance]

The difference (%) between the adjacent layers of each combination in total light transmittance was calculated based on the total light transmittance of each of the powder materials themselves in table 1.

[Sensory Evaluation (Transition Characteristics)]

Sensory evaluation concerning a natural color gradient was carried out. The evaluation was carried out visually by five persons. The basis for the evaluation was the number of persons for whom a color gradient looked natural. Specifically, when the number of persons for whom a color gradient looked natural was at least 4, an example showing such a color gradient was evaluated as "excellent"; when this number was 3, an example showing such a color gradient was evaluated as "good"; when this number was 2, an example showing such a color gradient was evaluated as "fair"; and when this number was at most 1, an example showing such a color gradient was evaluated as "failure".

TABLE 2

| Item | Example 1 | Example 2 | Example 3 | Example 4 | Example 5 | Example 6 | Example 7 |
|---|---|---|---|---|---|---|---|
| Combination of powder materials | A + B | A + C | B + C | A + B + C | B + D | C + D | D + E |
| Color difference ΔE | 1.15 | 4.17 | 3.24 | — | 5.38 | 2.22 | 4.02 |
| Difference in total light transmittance | 2.7 | 7.8 | 5.2 | — | 7.9 | 2.8 | 2.7 |
| Sensory evaluation (Transition characteristics) | excellent | fair | good | good | fair | excellent | excellent |

| Item | Example 8 | Example 9 | Example 10 | Comparative example 1 | Comparative example 2 | Comparative example 3 |
|---|---|---|---|---|---|---|
| Combination of powder materials | C + D + E | C + E | F + G | D | H + I | I + J |
| Color difference ΔE | — | 5.19 | 0.5 | — | 7.9 | 5.66 |
| Difference in total light transmittance | — | 5.4 | 1.8 | — | 3.8 | 3.2 |
| Sensory evaluation (Transition characteristics) | excellent | good | fair | failure | failure | failure |

C. (room temperature) for 10 minutes. The components of the colorant solution were as follows.

cerium acetate: 6.5 mass % erbium acetate: 6.5 mass % polyethylene glycol: 7.0 mass % distilled water: 80 mass %

As can be seen from table 2, it is found that setting the color difference ΔE between the powder materials to be prepared to be the adjacent layers in at most 5.5 enabled a glass-ceramic blank showing a natural color gradient to be obtained.

Combination of prepared powder materials each having a total light transmittance less than 33% as in example 10 led to slight deterioration in transition characteristics. At this time, there was a tendency for coloring to take a long time, and for coloring efficiency to lower.

The invention claimed is:

1. A method of producing a glass-ceramic blank formed by laminating plural layers, the method comprising:

preparing plural glass-ceramic powders, laminating the glass-ceramic powders, so that colors of any adjacent layers of the powders are the same as or approximate to each other, and so that said any adjacent layers are different in total light transmittance, and pressure-molding the laminated powders;

heating, at 500° C. to 800° C., a laminate obtained by the pressure molding to degrease the laminate;

immersing an entire of the laminate after the degreasing in a single-colored colorant solution, the colorant solution includes a metal ion as a coloring agent; and heat-treating at higher than 750° C. and lower than 1000° C. so that the coloring agent has a uniform concentration in the glass-ceramic blank, wherein in the pressure molding, a color difference between said any adjacent layers is at most 5.5, and the glass-ceramic blank being a block-like material configured for dental restoration.

2. The method according to claim 1, wherein in the pressure molding, a difference between said any adjacent layers in total light transmittance is 0.1% to 8%.

3. The method according to claim 1, wherein the total light transmittance of each of the layers is at least 33%.

4. The method according to claim 1, wherein the metal ion is erbium or cerium.

* * * * *